US012042170B2

(12) United States Patent
Elmouelhi et al.

(10) Patent No.: US 12,042,170 B2
(45) Date of Patent: Jul. 23, 2024

(54) ADD-ON SHEATH

(71) Applicant: EvolutionMedVentures LLC, Plymouth, MN (US)

(72) Inventors: Ahmed M. Elmouelhi, Plymouth, MN (US); Sameer Gafoor, Mercer Island, WA (US)

(73) Assignee: EVOLUTIONMEDVENTURES LLC, Plymouth, MN (US)

( * ) Notice: Subject to any disclaimer, the term of this patent is extended or adjusted under 35 U.S.C. 154(b) by 445 days.

(21) Appl. No.: 16/871,299

(22) Filed: May 11, 2020

(65) Prior Publication Data

US 2020/0352598 A1  Nov. 12, 2020

Related U.S. Application Data

(60) Provisional application No. 62/846,733, filed on May 12, 2019.

(51) Int. Cl.
*A61B 17/34* (2006.01)
*A61B 17/00* (2006.01)

(52) U.S. Cl.
CPC ........... *A61B 17/3423* (2013.01); *A61B 2017/00336* (2013.01); *A61B 2017/00477* (2013.01); *A61B 2217/007* (2013.01)

(58) Field of Classification Search
CPC ...... A61B 17/3423; A61B 2017/00336; A61B 2017/00477; A61B 2217/007; A61B 1/00135; A61B 2017/3447; A61M 25/0662; A61M 25/0023; A61M 25/0097; A61M 2025/0025; A61M 2025/0177
See application file for complete search history.

(56) References Cited

U.S. PATENT DOCUMENTS

| | | | |
|---|---|---|---|
| 5,106,368 A | 4/1992 | Uldall et al. | |
| 5,207,649 A | 5/1993 | Aruny | |
| 5,250,038 A | 10/1993 | Melker et al. | |
| 5,643,175 A * | 7/1997 | Adair | A61B 1/00142 600/156 |
| 6,183,443 B1 | 2/2001 | Kratoska et al. | |
| 6,190,349 B1 | 2/2001 | Ash et al. | |
| 6,461,321 B1 | 10/2002 | Quinn | |
| 6,517,518 B2 | 2/2003 | Nash et al. | |
| 6,579,264 B1 | 6/2003 | Rossi | |
| 6,866,625 B1 * | 3/2005 | Ayre | A61M 60/221 600/16 |
| 7,155,272 B2 | 12/2006 | Yamaguchi et al. | |
| 7,569,029 B2 | 8/2009 | Clark | |
| 8,317,715 B2 | 11/2012 | Belleville et al. | |

(Continued)

*Primary Examiner* — Richard G Louis
(74) *Attorney, Agent, or Firm* — Fredrikson & Byron, P.A.

(57) ABSTRACT

A sheath assembly includes a first sheath, a second sheath, and an attachment mechanism. The attachment mechanism secures the second sheath to the first sheath such that a first portion of a second sheath outer surface interfaces with a portion of a first sheath outer surface. The second sheath is configured to transition between an expanded state and a collapsed state such that the profile of the sheath assembly can be reduced when the second sheath is in the collapsed state. This can allow the sheath assembly to become more compact, for instance, during insertion, but yet expandable, for instance, once in place within a patient to suitably accommodate an instrument within the second sheath.

15 Claims, 9 Drawing Sheets

(56) References Cited

U.S. PATENT DOCUMENTS

| | | |
|---|---|---|
| 8,517,978 B2 | 8/2013 | Clark |
| 8,613,706 B2 | 12/2013 | Langston |
| 8,808,227 B2 | 8/2014 | Zawacki et al. |
| 9,332,914 B2 | 5/2016 | Langston |
| 9,339,633 B2 | 5/2016 | Tchirikov |
| 9,889,274 B2 | 2/2018 | Mallin |
| 10,667,702 B2 | 6/2020 | Langston |
| 10,737,008 B2 | 8/2020 | Corbett et al. |
| 10,953,205 B2 | 3/2021 | Korkuch |
| 2001/0012946 A1* | 8/2001 | MacKenzie ........ A61B 17/3421 606/198 |
| 2001/0031979 A1 | 10/2001 | Ricci |
| 2002/0058857 A1* | 5/2002 | Smith .................... A61B 17/29 600/153 |
| 2002/0099326 A1 | 7/2002 | Wilson et al. |
| 2003/0032941 A1 | 2/2003 | Boyle et al. |
| 2003/0130564 A1* | 7/2003 | Martone ............ A61B 1/00071 600/139 |
| 2003/0212373 A1 | 11/2003 | Hall et al. |
| 2004/0230096 A1* | 11/2004 | Stefanchik ......... A61B 1/00073 600/128 |
| 2006/0200000 A1* | 9/2006 | Sato .................... A61B 1/0057 600/146 |
| 2006/0235458 A1* | 10/2006 | Belson ............... A61B 1/00135 606/191 |
| 2014/0275795 A1 | 9/2014 | Little et al. |
| 2016/0051384 A1* | 2/2016 | Patel ......................... C22F 1/18 148/668 |
| 2016/0067444 A1 | 3/2016 | Allen et al. |
| 2019/0151144 A1 | 5/2019 | Burnett et al. |
| 2020/0046201 A1* | 2/2020 | Ho ......................... A61B 1/005 |
| 2020/0289794 A1 | 9/2020 | Fantuzzi et al. |

* cited by examiner

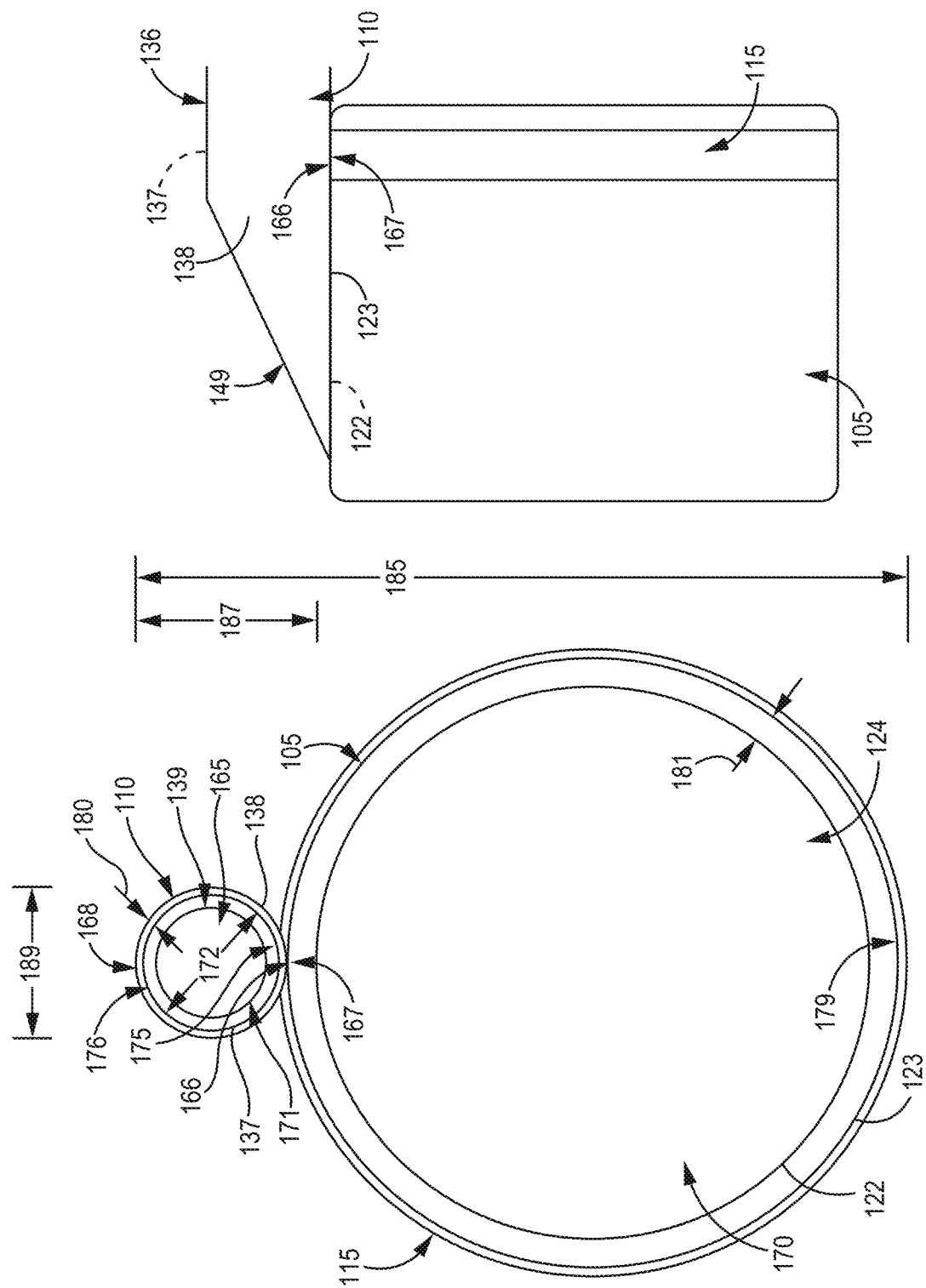

ADD-ON SHEATH

RELATED APPLICATION

This application claims priority to U.S. provisional patent application No. 62/846,733 filed on May 12, 2019.

TECHNICAL FIELD

This disclosure generally relates to sheaths, sheath assemblies, add-on sheath kits, and related systems and methods. Certain such embodiments are described herein in the context of medical percutaneous interventional and diagnostic procedures as exemplary types of applications in which the sheaths, sheath assemblies, add-on sheath kits, and related systems and methods can be used.

BACKGROUND

Medical diagnostic and interventional procedures are performed to assess, and when necessary take action to address, one or more conditions at a variety of anatomical locations. In many such procedures, an intravascular device, such as a catheter, is inserted into a patient's vessel at an access site on the patient and traversed through the vessel to the particular region of interest.

In one such example where the cardiac region is the region of interest, medical diagnostic and interventional procedures commonly require two separate access sites on the patient. Generally, such procedures use one access site at the Femoral Artery and another, separate access site at either Radial Artery, the Contralateral Femoral Artery, or other similarly sized vessels (e.g., Subclavian Artery). These separate access sites are then used to insert the necessary diagnostic instrument(s) and interventional instrument(s) into the patient and separately guide these instruments to the cardiac region of interest. Because such procedures commonly utilize multiple instruments at the cardiac region of interest, the separate access sites at the patient can allow for the capacity needed (e.g., via both of the Femoral and Radial Arteries) to traverse the instrument payloads to the cardiac region of interest.

SUMMARY

In general, various embodiments relating to sheaths, sheath assemblies, add-on sheath kits, and related systems and methods are disclosed herein. In particular, embodiments disclosed herein can facilitate medical diagnostic and interventional procedures via a single access site at the patient. Thus, embodiments disclosed herein can facilitate a percutaneous medical interventional procedure using a single (e.g., Femoral Artery) access site at the patient, thereby reducing the number of access sites needed for such procedure by eliminating the need for a second access site (e.g., eliminating the need for a Radial Artery access site) and, in turn, eliminating risks associated with a second access site and reducing overall procedure time. As a result, embodiments disclosed herein can allow for less invasive procedures and preserve the second access site for any future procedures. At the same time, embodiments disclosed herein can provide these advantages while maintaining the functionality that would ordinarily be provided via a second access site.

Various embodiments described herein can provide a sheath that is configured to transition between an expanded state and a collapsed state. Such a sheath can allow for a reduced profile in the collapsed state, for instance, while the sheath is being traversed through a vessel, while also providing the ability to accommodate one or more instruments therein when in the expanded state, for instance once the sheath has reached the region of interest. This sheath can be configured to be added on to another sheath by securing the two sheaths to one another via one or more attachment mechanisms. In this way, the add-on sheath configured to transition between expanded and collapsed states can be used with another sheath already intended for use at one access site that has limited available space.

One embodiment includes a sheath assembly. This sheath assembly embodiment includes a first sheath, a second sheath, and an attachment mechanism. The first sheath includes a first sheath first end portion, a first sheath second end portion opposite the first sheath first end portion, a first sheath inner surface, and a first sheath outer surface opposite the first sheath inner surface. The first sheath inner surface defines a first sheath lumen extending along a first sheath longitudinal axis between the first sheath first end portion and the first sheath second end portion. The second sheath includes a second sheath first end portion, a second sheath second end portion opposite the second sheath first end portion, a second sheath inner surface, and a second sheath outer surface opposite the second sheath inner surface. The second sheath inner surface defines a second sheath lumen extending along a second sheath longitudinal axis between the second sheath first end portion and the second sheath second end portion. The attachment mechanism secures the second sheath to the first sheath such that a first portion of the second sheath outer surface interfaces with a portion of the first sheath outer surface. The second sheath includes a second portion of the second sheath outer surface that is opposite the first portion of the second sheath outer surface. The second sheath is configured to transition between an expanded state and a collapsed state. The second portion of the second sheath outer surface is closer to the first sheath outer surface in the collapsed state than in the expanded state.

In a further embodiment of the sheath assembly, the sheath assembly is configured to be inserted within a vessel lumen. In this further embodiment, the second sheath is configured to transition from the expanded state to the collapsed state when the second portion of the second sheath outer surface comes into contact with a vessel wall defining the vessel lumen. In particular, the second sheath can be biased to the expanded state, and the second sheath can be configured such that the bias to the expanded state is overcome when the second portion of the second sheath outer surface comes into contact with the vessel wall.

Another embodiment includes an add-on sheath kit comprising a packaging container defining a closed interior volume. In this embodiment, the closed interior volume of the packaging container includes a sheath and an attachment mechanism. The sheath includes a sheath first end portion, a sheath second end portion opposite the sheath first end portion, a sheath inner surface, and a sheath outer surface opposite the sheath inner surface. The sheath inner surface defines a sheath lumen extending along a sheath longitudinal axis between the sheath first end portion and the sheath second end portion. The attachment mechanism includes a band attached to a first portion of the sheath outer surface and extending out from the first portion of the sheath outer surface away from the sheath. The sheath includes a second portion of the sheath outer surface that is opposite the first portion of the sheath outer surface. The sheath is configured to transition between an expanded state and a collapsed state. The second portion of the sheath outer surface is closer to the first portion of the sheath outer surface in the collapsed state than in the expanded state.

An additional embodiment includes a method of using a sheath assembly. This method embodiment includes the steps of securing a second sheath to a first sheath via an attachment mechanism such that a first portion of a second sheath outer surface interfaces with a first sheath outer surface, and inserting a guidewire to a region of interest within a patient. This method embodiment includes the step of placing the first sheath over the guidewire and inserting the first sheath and the second sheath into the patient through a single access site at the patient. This method embodiment also includes the step of transitioning the second sheath from an expanded state to a collapsed state upon inserting the second sheath into the patient. The second sheath can collapse to the collapsed state in a direction toward the first sheath. This method embodiment further includes the step of inserting an instrument through the second sheath and causing the second sheath to transition from the collapsed state to the expanded state.

The details of one or more examples are set forth in the accompanying drawings and the description below. Other features, objects, and advantages will be apparent from the description and drawings.

BRIEF DESCRIPTION OF THE DRAWINGS

The following drawings are illustrative of particular embodiments of the present invention and therefore do not limit the scope of the invention. The drawings are intended for use in conjunction with the explanations in the following description. Embodiments of the invention will hereinafter be described in conjunction with the appended drawings, wherein like numerals denote like elements. The drawings are not necessarily to scale, though certain embodiments can include one or more components at the scale shown.

FIGS. 4A and 4B show the second sheath, of the sheath assembly embodiment of FIG. 1, in an exemplary expanded state. FIG. 4A shows a cross-sectional view of the sheath assembly, taken along line B-B in FIG. 3, with the second sheath in the exemplary expanded state. FIG. 4B shows a close-up side elevational view of the sheath assembly, with the second sheath in the exemplary expanded state.

FIG. 5A shows a cross-sectional view of the sheath assembly, taken along line A-A in FIG. 2, with the second sheath in the exemplary collapsed state. FIG. 5B shows a close-up side elevational view of the sheath assembly, with the second sheath in the exemplary collapsed state.

DETAILED DESCRIPTION

The following detailed description is exemplary in nature and is not intended to limit the scope, applicability, or configuration of the invention in any way. Rather, the following description provides some practical illustrations for implementing embodiments of the present invention. Examples of constructions, materials, and/or dimensions are provided for selected elements. Those skilled in the art will recognize that many of the noted examples have a variety of suitable alternatives.

Figure 1:
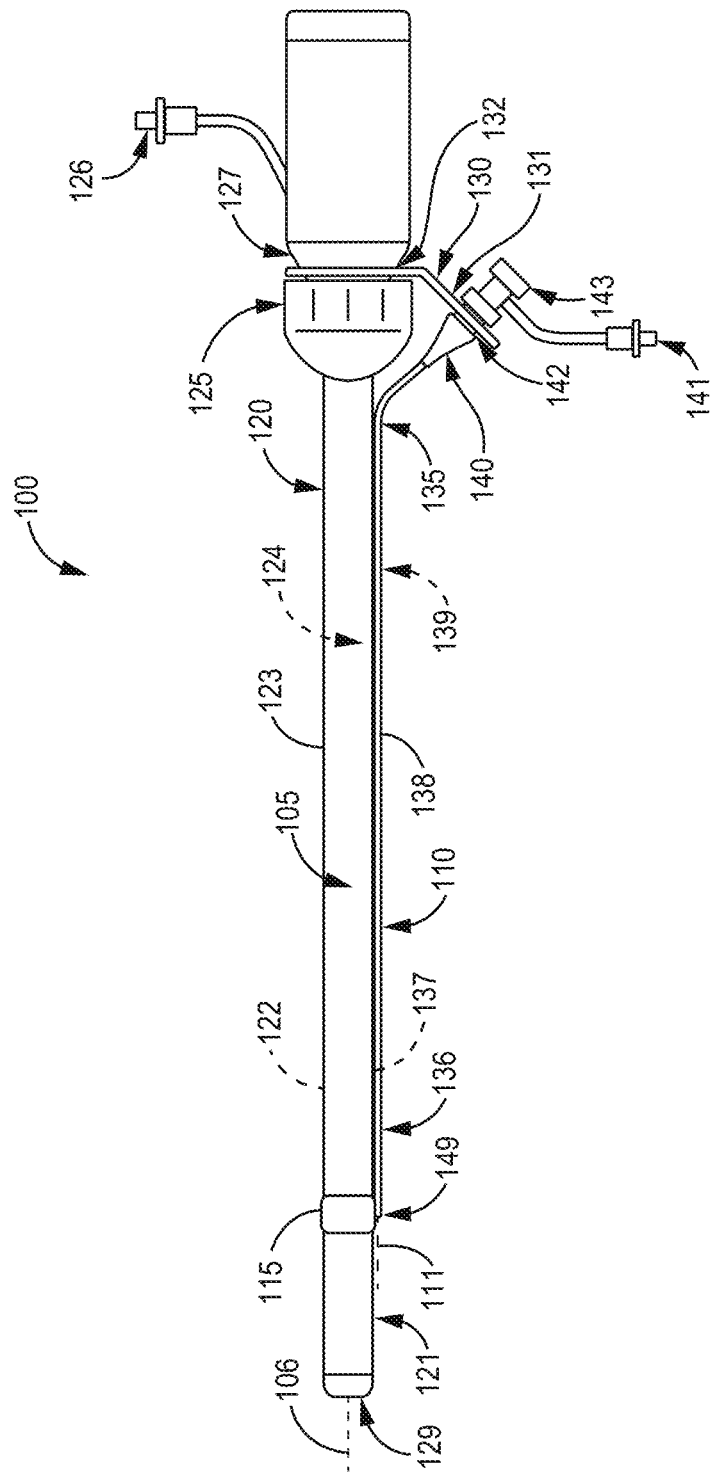
FIG. 1 is a side elevational view of an embodiment of a sheath assembly.

FIG. 1 shows a side elevational view of an exemplary embodiment of a sheath assembly 100. The sheath assembly 100 includes a first sheath 105 and a second sheath 110. As shown here, the first sheath 105 and the second sheath 110 are secured together by an attachment mechanism 115 in a stacked arrangement such that the first sheath 105 and the second sheath 110 are arranged side-by-side with their respective outer surfaces interfacing with one another. In this stacked arrangement, a first sheath longitudinal axis 106, of the first sheath 105, is offset from and generally parallel to a second sheath longitudinal axis 111, of the second sheath 110.

In the sheath assembly 100, the first sheath 105 includes a first sheath first end portion 120, a first sheath second end portion 121, a first sheath inner surface 122, and a first sheath outer surface 123. The first sheath second end portion 121 is opposite the first sheath first end portion 120. The first sheath outer surface 123 is opposite the first sheath inner surface 122. The first sheath inner surface 122 defines a first sheath lumen 124 extending along the first sheath longitudinal axis 106 between the first sheath first end portion 120 and the first sheath second end portion 121. The first sheath second end portion 121 can include a first sheath opening 129, for instance to allow an instrument and/or guide wire inserted within the first sheath lumen 124 to extend out from the first sheath 105 at the first sheath opening 129.

At the first sheath first end portion 120 is a proximal hub 125. The proximal hub 125 can be open to, and in communication with, the first sheath lumen 124. As such, the proximal hub 125 can be configured to facilitate access to the first sheath lumen 124. For example, the proximal hub 125 can be configured to receive one or more diagnostic or interventional instruments (e.g., a catheter) that are to be used for a procedure and delivered through the first sheath lumen 124. As shown here, the proximal hub 125 includes a flush port 126 and a clip attachment interface 127. The flush port 126 is configured to facilitate fluid communication with the first sheath lumen 124 and/or a diagnostic and/or interventional instrument within the first sheath lumen 124. The clip attachment interface 127 is configured to receive a clip 130 for securing proximal end portions of the sheaths 105, 110.

Also in the sheath assembly 100, the second sheath 110 includes a second sheath first end portion 135, a second sheath second end portion 136, a second sheath inner surface 137, and a second sheath outer surface 138. The second sheath second end portion 136 is opposite the second sheath first end portion 135. The second sheath outer surface 138 is opposite the second sheath inner surface 137. The second sheath inner surface 137 defines a second sheath lumen 139 extending along the second sheath longitudinal axis 111 between the second sheath first end portion 135 and the second sheath second end portion 136. The second sheath second end portion 136 can include a second sheath opening 149, for instance to allow an instrument and/or guide wire inserted within the second sheath lumen 139 to extend out from the second sheath 110 at the second sheath opening 149. As shown in FIG. 1, the first sheath 105 and the second sheath 110 can be of a substantially similar length between their respective end portions 120, 135 and 121, 136. In particular, the first sheath first end portion 120 and the second sheath first end portion 135 can terminate at a similar proximal location, and the first sheath second end portion 121 and the second sheath second end portion 136 an terminate at a similar distal location (e.g., in FIG. 1, the second sheath second end portion 136 terminates just short of the first sheath second end portion 121 (e.g., 1-10 cm, such as 3-5 cm, short of the first sheath second end portion 121)).

At the second sheath first end portion 135 is a proximal hub 140. The proximal hub 140 can be open to, and in communication with, the second sheath lumen 139 As such, the proximal hub 140 can be configured to facilitate access to the second sheath lumen 139. For example, the proximal hub 140 can be configured to receive one or more diagnostic or interventional instruments (e.g., a catheter) that are to be used for a procedure and delivered through the second sheath lumen 139. As shown here, the proximal hub 140 includes a flush port 141, a clip attachment interface 142, and an instrument insertion port 143. The flush port 141 is spaced apart from the instrument insertion port 143 and in communication with the second sheath lumen 139. As such, the flush port 141 is configured to facilitate fluid communication with the second sheath lumen 139 and/or a diagnostic and/or interventional instrument within the second sheath lumen 139. The clip attachment interface 142 is configured to receive the clip 130 for securing proximal end portions of the sheaths 105, 110. As shown in the illustrated embodiment, the clip attachment interface 142 includes a recessed slot formed at the proximal hub 140 and configured to create an interference fit with the clip 130, though in other embodiments the clip attachment interface 142 can include other types of structures configured to receive the clip 130. The instrument insertion port 143 is in communication with the second sheath lumen 139, and the instrument insertion port 143 is configured to receive a diagnostic and/or interventional instrument (e.g., a guidewire and a catheter) thereat and pass this instrument into the second sheath lumen 139.

The clip 130 is configured to secure the second sheath 110 to the first sheath 105. Specifically, the clip 130 is configured to secure the hub 125 to the hub 140. The clip 130 can include a first clip securement portion 131 configured to receive the second sheath 110 and a second clip securement portion 132, spaced apart from the first clip securement portion 131, configured to receive the first sheath 105. The clip attachment interface 142 is configured to receive the first clip securement portion 131 and the clip attachment interface 127 is configured to receive the second clip securement portion 132 so as to secure the proximal hub 140 to the proximal hub 125. In the illustrated embodiment, the first clip securement portion 131 is non-parallel to the second clip securement portion 132, with the first clip securement portion 131 extending at an angle between fifteen and eighty five degrees (e.g., between twenty five and seventy five degrees, between forty and sixty degrees) from a plane on which the second clip securement portion 132 lies. Each clip securement portion 131, 132 can include an aperture that secures around at least a portion of (e.g., all of) each respective clip attachment interface 142, 127.

Figure 2:
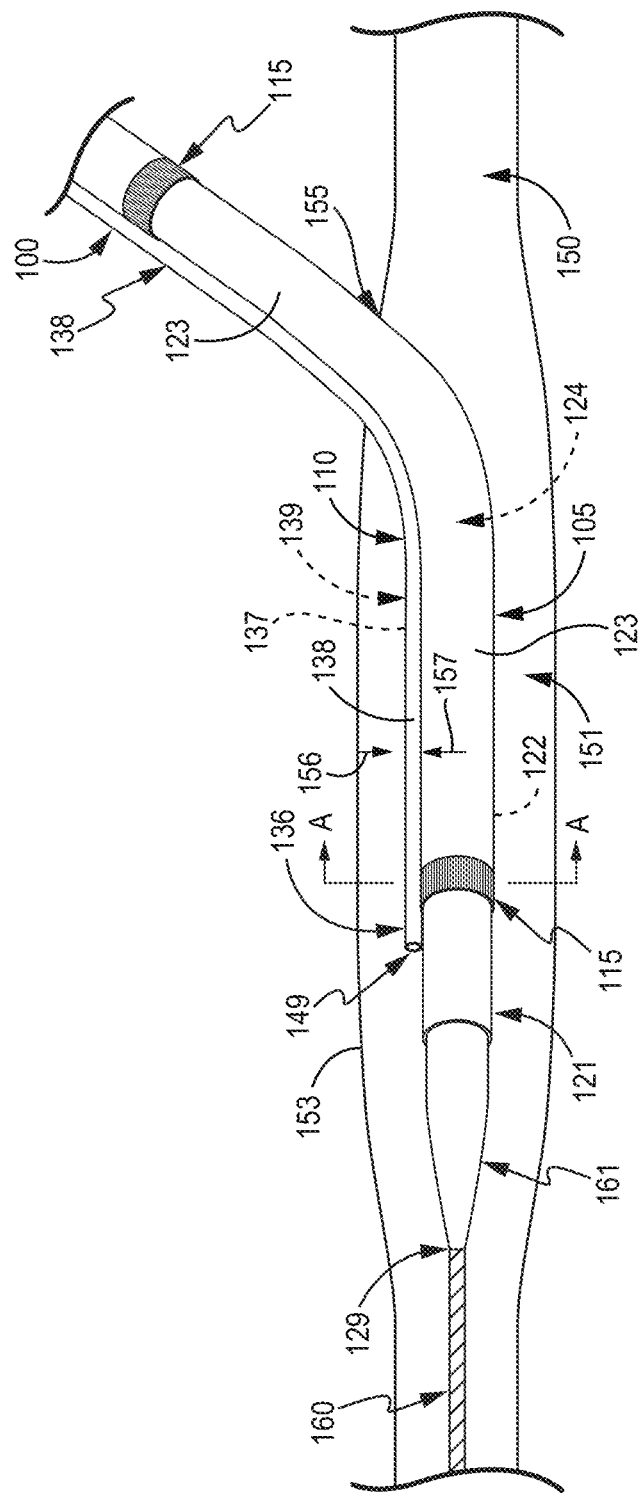
FIG. 2 is a side elevational view of a portion of the sheath assembly embodiment of FIG. 1 being inserted into a vessel lumen, with a second sheath of the sheath assembly in a collapsed state.
Figure 3:
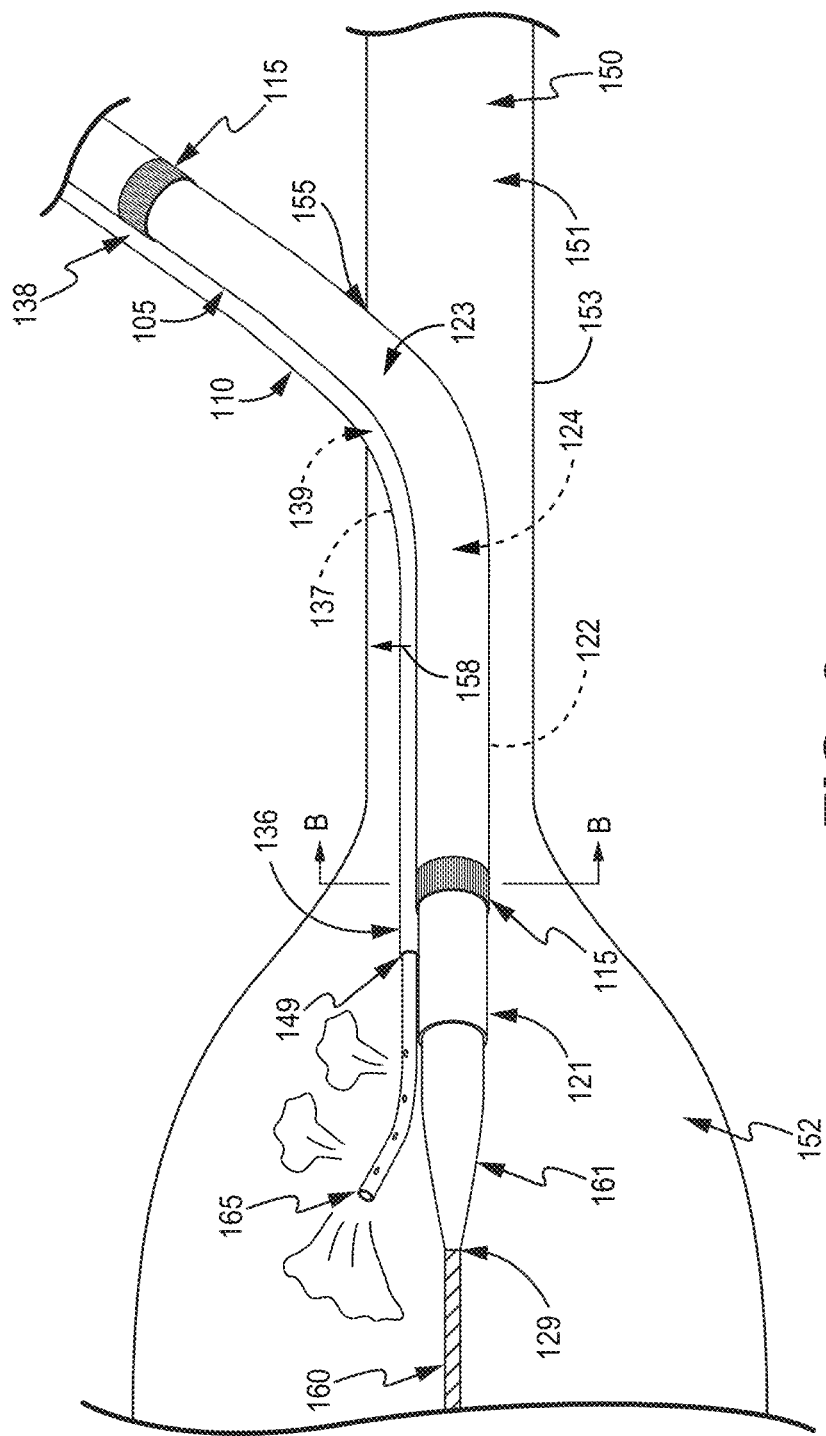
FIG. 3 is a side elevational view of a portion of the sheath assembly embodiment of FIG. 1 at a region of interest in the vessel lumen, with the second sheath of the sheath assembly in an expanded state.

FIGS. 2 and 3 show a portion of the sheath assembly 100 deployed within a vessel 150, such as a blood vessel of a patient. As shown here, the sheath assembly 100, with both the first sheath 105 and the second sheath 110, is inserted into the vessel 150 via a single access site 155. In one exemplary application, the vessel 150 can be the Femoral Artery and the sheath assembly 100 can be inserted into the Femoral Artery via the single access site 155. In this way, both the first sheath 105 and the second sheath 110 can facilitate a percutaneous diagnostic and/or interventional procedure using the single access site 155 and thereby eliminate risks and complications associated with a second access site for deploying one of the sheaths.

To facilitate deployment of the sheath assembly 100 via the single access site 155, the second sheath 110 can be configured to transition between an expanded state and a collapsed state. In this way, the second sheath 110 can allow the sheath assembly 100 to have a reduced profile, when the second sheath 110 is in the collapsed state, for instance, while the sheath assembly 100 is being inserted in and traversed through the vessel 150. And, in this way, the second sheath 110 can also provide the ability to accommodate one or more diagnostic and/or interventional instrument(s) (e.g., a diagnostic or auxiliary catheter) within the second sheath 110 when the second sheath 110 is in the expanded state, for instance once the sheath has reached a region of interest 152. FIG. 2 illustrates a side elevational view of the portion of the sheath assembly 100 being inserted into a vessel lumen 151 of the vessel 150 with the second sheath 110 in a collapsed state. FIG. 3 illustrates a side elevational view of the portion of the sheath assembly 100 having reached the region of interest 152 in the vessel lumen 151 and now with the second sheath 110 in an expanded state.

As shown, the sheath assembly 100 can be inserted within the vessel lumen 151 and traversed through the vessel 150 to the region of interest 152 using a guidewire 160. The first sheath 105 can be placed onto the guidewire 160 such that the guidewire 160 is received within the first sheath lumen 124. The sheath assembly 100 can then be advanced into the vessel lumen 151 through the single access site 155 over the guidewire 160 at the first sheath 105. In some embodiments, the first sheath 105 can include an introducer 161 at the first sheath second end portion 121 to assist in deploying the sheath assembly 100 into, and through, the vessel lumen 151.

As noted, the second sheath 110 can be configured to transition between an expanded state and a collapsed state. In the illustrated embodiment, the second sheath 110 can be biased to the expanded state, and the second sheath 110 can be configured to transition from the expanded state to the collapsed state when the second sheath outer surface 138 comes into contact with a vessel wall 153 defining the vessel lumen 151. In this way, the second sheath 110 can be configured such that the bias to the expanded state is overcome when the second sheath outer surface 138 comes into contact with the vessel wall 153. Therefore, in such embodiments, when the sheath assembly 100 is being inserted within and traversed through the vessel lumen 151, as in FIG. 2, the second sheath 110 can generally be in contact with the vessel wall 153 and thus be in a collapsed state. Also, in such embodiments, the sheath assembly 100 can be configured such that the second sheath 110 is configured to transition from the expanded state to the collapsed state, and be maintained in the collapsed state, while the first sheath 105 is maintained in a first sheath expanded state. This can maintain the first sheath lumen 124 at its designed capacity, for example, so as to be useful in instances where the first sheath 105 receives the guidewire 160 for advancing the sheath assembly 110 to the region of interest 152. In some cases, the first sheath 105 may not be collapsible, though certain embodiments can include a first sheath that is configured to transition between collapsed and expanded states.

The second sheath 110 can include one or more features to facilitate transitioning between expanded and collapsed states. For example, the first sheath 105 can have a first hardness, X, and the second sheath 110 can have a second hardness, Y, where the first hardness, X, of the first sheath 105 is greater than the second hardness, Y, of the second sheath 110. As examples, the first sheath 105 can have a Rockwell hardness between 70A and 100A, such as between 80A and 90A, and the second sheath 110 can have a Rockwell hardness between 30A and 70A, such as between 40A and 60A. In this way, the second sheath 110 can be configured to be collapsible upon the forces imparted on the second sheath 110 by each of the harder first sheath 105 and the vessel wall 153. More specifically, as the second sheath 110 comes into contact with the vessel wall 153, the vessel wall 153 can impart a force 156 in a first direction on the second sheath outer surface 138 while the harder first sheath 105 can impart a force 157 in a second, opposite direction on the second sheath outer surface 138 causing the second sheath to collapse between the first force 156 and the second force 157. In this case, the second sheath 110 will collapse in a direction toward the first sheath 105. Accordingly, the second sheath 110 is able to transition from the expanded state to the collapsed state and thereby render the sheath assembly 100 more compact within the vessel lumen 151.

As noted, the second sheath 110 can have one or more dimensions and/or include one or more materials (e.g., that contribute to the hardness or stiffness of the second sheath 110) that allow it to collapse when being inserted into, and traversed through, the vessel lumen 151. For example, the second sheath 110 can include a wall thickness, defined between the second sheath outer surface 138 and the second sheath inner surface 137, that is less than a wall thickness of the first sheath 105, defined between the first sheath outer surface 123 and the first sheath inner surface 122. As one example, the wall thickness of the second sheath can be between 0.1 mm and 1.5 mm, such as between 0.15 mm and 0.75 mm (e.g., between 0.15 mm and 0.5 mm) or between 0.25 mm and 0.5 mm. As another example, the second sheath 110 can be made of a collapsible polymer or mesh material that is configured to collapse under forces exerted on it by the vessel wall 153 (e.g., a vessel wall of the Femoral Artery). For instance, the second sheath 110 can include biocompatible polyurethane (e.g., Pellethane™). Depending on the particular application, the combination of material including biocompatible polyurethane along with the hardness and/or wall thickness of the second sheath 110 relative to the first sheath 105 can allow the second sheath 110 to transition from the expanded state to the collapsed state when inserted into, and traversed through, the vessel lumen 151 as a result of contact with the vessel wall 153.

To allow the second sheath 110 to collapse to its fullest extent, no hardware (e.g., instrument, guidewire, etc.) may be present within the second sheath lumen 139 when the sheath assembly 100 is inserted into and traversed through the vessel lumen 151, as in FIG. 2. Then, once the sheath assembly 100 has reached the region of interest 152, as in FIG. 3, one or more hardware components (e.g., a guidewire, and/or a diagnostic and/or interventional instrument, such as a diagnostic or auxiliary catheter) can be inserted within the second sheath lumen 139.

The second sheath 110 can be configured to transition from the collapsed state, as in FIG. 2 when the second sheath 110 is in contact with the vessel wall 153, toward the expanded state, as in FIG. 3, upon insertion of a hardware component (e.g., a rigid hardware component) within the second sheath lumen 139. FIG. 3 shows a catheter 165 (e.g., a pigtail catheter) inserted within the second sheath lumen 139 and extending out from the second sheath opening 149 at the region of interest 152. Inserting the hardware component, such as the catheter 165, within the second sheath lumen 139 can impart a force 158 in the second direction on the second sheath 110 causing the second sheath 110 to expand out from the collapsed state. Thus, this force 158 imparted by the catheter 165 on the second sheath 110 in the second direction can counteract some, or all, of the force 156 applied by the vessel wall 153 allowing the second sheath 110 to transition from the collapsed state, as in FIG. 2 when the second sheath 110 is in contact with the vessel wall 153, toward, or to, the expanded state, as in FIG. 3.

Depending on the particular application, such as the hardware inserted within the second sheath lumen 139, the second sheath 110 may only partially transition from the collapsed state to the expanded state (e.g., the second sheath 110 extends out from the first sheath 105 to a lesser extent than when the sheath assembly 100 is not within the vessel 150) when a hardware component is present within the second sheath lumen 139, as in FIG. 3. Because the second sheath 110 can be configured to collapse when in contact with the vessel wall 153, the force 156 applied by the vessel wall 153 can continue to counteract the force 158 and thereby constrain the expansion of the second sheath 110 when the hardware component, such as the catheter 165, is present within the second sheath lumen 139. Accordingly, the second sheath 110 can be configured to transition from the collapsed state toward the expanded state only to the extent needed to accommodate the hardware component within the second sheath lumen 139, thereby keeping a minimum necessary profile of the sheath assembly 100 even when the second sheath 110 is actively being used during a procedure. In this way, the second sheath 110, configured to transition between expanded and collapsed states, can facilitate a reduced profile of the sheath assembly 100 both during insertion and placement as well as during usage of the second sheath 110 during a procedure. As a result, the sheath assembly 100 can be capable of use via the single access site 155.

FIGS. 4A-5B illustrate exemplary expanded and collapsed states of the second sheath 110.

4A and 4B show the second sheath 110 in an exemplary expanded state. FIG. 4A shows a cross-sectional view of the sheath assembly 100, taken along line B-B in FIG. 3, with the second sheath 110 in the expanded state. FIG. 4B shows a close-up side elevational view of the sheath assembly 100 with the second sheath 110 in the expanded state. As noted, the second sheath 110 can be in an expanded state (e.g., transition from the collapsed state to an expanded state) when the catheter 165, or other hardware component, is within the second sheath lumen 139 as shown in FIG. 4A.

The attachment mechanism 115 can secure the second sheath 110 to the first sheath 105 such that a first portion 166 of the second sheath outer surface 138 interfaces with a portion 167 of the first sheath outer surface 123. For the illustrated arrangement, the attachment mechanism 115 can be said to secure the second sheath 110 to the first sheath 105 in a stacked arrangement. As shown, the attachment mechanism 115 is located between the second sheath outer surface 138 and the first sheath outer surface 123, and, in particular, the attachment mechanism 115 is located between the first portion 166 of the second sheath outer surface 138 and the portion 167 of the first sheath outer surface 123. The second sheath 110 also has a second portion 168 of the second sheath outer surface 138 that is opposite the first portion 166 of the second sheath outer surface 138. The second portion 168 can be a portion of the second sheath outer surface 138 that comes into contact with the vessel wall 153 defining the vessel lumen 151. The second sheath 110 can also include a first portion 175 of the second sheath inner surface 137 adjacent to the first portion 166 of the second sheath outer surface 138 and a second portion 176 of the second sheath inner surface 137 adjacent to the second portion 168 of the second sheath outer surface 138.

In the illustrated embodiment, the attachment mechanism 115 does not pass over the second sheath 110, but rather the attachment mechanism 115 is generally in contact with the second sheath 110 at only the first portion 166 of the second sheath outer surface 138 interfacing with the first sheath outer surface 123. This arrangement of the attachment mechanism 115 can be useful in securing the second sheath 110 to the first sheath 105 while not constraining the ability of the second sheath 110 to transition between the expanded and collapsed states.

In the illustrated embodiment, the attachment mechanism 115 is in the form of an elastic band. The elastic band shown here is attached to the first portion 166 of the second sheath outer surface 138 and extends around at least a portion of the first sheath outer surface 123. As shown, the second portion 168 of the second sheath outer surface 138 can be free of the elastic band, which as noted can facilitate the transitioning of the second sheath 110 between the expanded and collapsed states. In the illustrated embodiment, the elastic band extends around the entire first sheath outer surface 123 for a particular longitudinal length along the first sheath longitudinal axis 106. In other embodiments, the attachment mechanism 115 can take other suitable forms configured to secure the first and second sheaths 105, 110 to one another. For example, the attachment mechanism 115 could include an adhesive placed in between the first portion 166 of the second sheath outer surface 138 and the portion 167 of the first sheath outer surface 123. As another example, the attachment mechanism 115 could include a welded, or heat melted, connection between the first portion 166 of the second sheath outer surface 138 and the portion 167 of the first sheath outer surface 123.

As shown in FIGS. 4A and 4B, the first sheath lumen 124 defines a first sheath lumen cross-sectional area 170, and the second sheath lumen 139 defines an expanded state second sheath lumen cross-sectional area 171 when the second sheath 110 is in the expanded state as shown here. The first sheath lumen cross-sectional area 170 can be greater than the expanded state second sheath lumen cross-sectional area 171. The second sheath 110 being smaller than the first sheath 105 can be useful in facilitating use at the single access site 155, as described above. For example, depending of the application of the sheath assembly 100, the expanded state second sheath lumen cross-sectional area 171 can be between 5% and 75% of the first sheath lumen cross-sectional area 170, such as between 10% and 50%, 10% and 40%, 10% and 30%, or 10% and 20% of first sheath lumen cross-sectional area 170. The expanded state second sheath lumen cross-sectional area 171 can include a diameter 172 between 1 mm and 5 mm, for example between 1.5 mm and 4.5 mm, 2 mm and 4.5 mm, or 2.5 mm and 4.0 mm. The relative size of the first and second sheaths 105, 110 can be important in various applications in both allowing for the necessary instruments to be deployed in a procedure while at the same time minimizing a profile of the sheath assembly 100 so as to be deployable via the single access site 155.

As shown in FIG. 4A, the second sheath 110 can have a first cross-sectional height 187 in the expanded state defined from the second portion 168 of the second sheath outer surface 138 to the first portion 166 of the second sheath outer surface 138. As also shown in FIG. 4A, the sheath assembly 100 can have a first overall cross-sectional height 185 defined from the second portion 168 of the second sheath outer surface 138 to an end portion 179 of the first sheath outer surface 123. The first cross-sectional height 187 of the second sheath 110 and the first overall cross-sectional height 185 of the sheath assembly 100 are each measured in a direction perpendicular to the longitudinal axes 106, 111. For example, the second sheath 110 can have the first cross-sectional height 187 in the expanded state between 1 mm to 5 mm, such as between 2 mm to 4 mm, or 2 mm to 3.5 mm, and the first overall cross-sectional height 185 of the sheath assembly 100, when the second sheath 110 is in the expanded state, can be between 7 mm and 12 mm, such as between 8 mm and 11 mm, or 7.5 mm and 10.5 mm.

And, as noted previously and shown in FIG. 4A, in some embodiments, to help configure the second sheath 110 to transition between the expanded and collapsed states, second sheath 110 can have a wall thickness 180 that is less than a wall thickness 181 of the first sheath 105. The wall thickness 180 of the second sheath 110 can be defined between the second sheath outer surface 138 and the second sheath inner surface 137, and the wall thickness 181 of the first sheath 105 can be defined between the first sheath outer surface 123 and the first sheath inner surface 122.

Figures 5A, 5B:
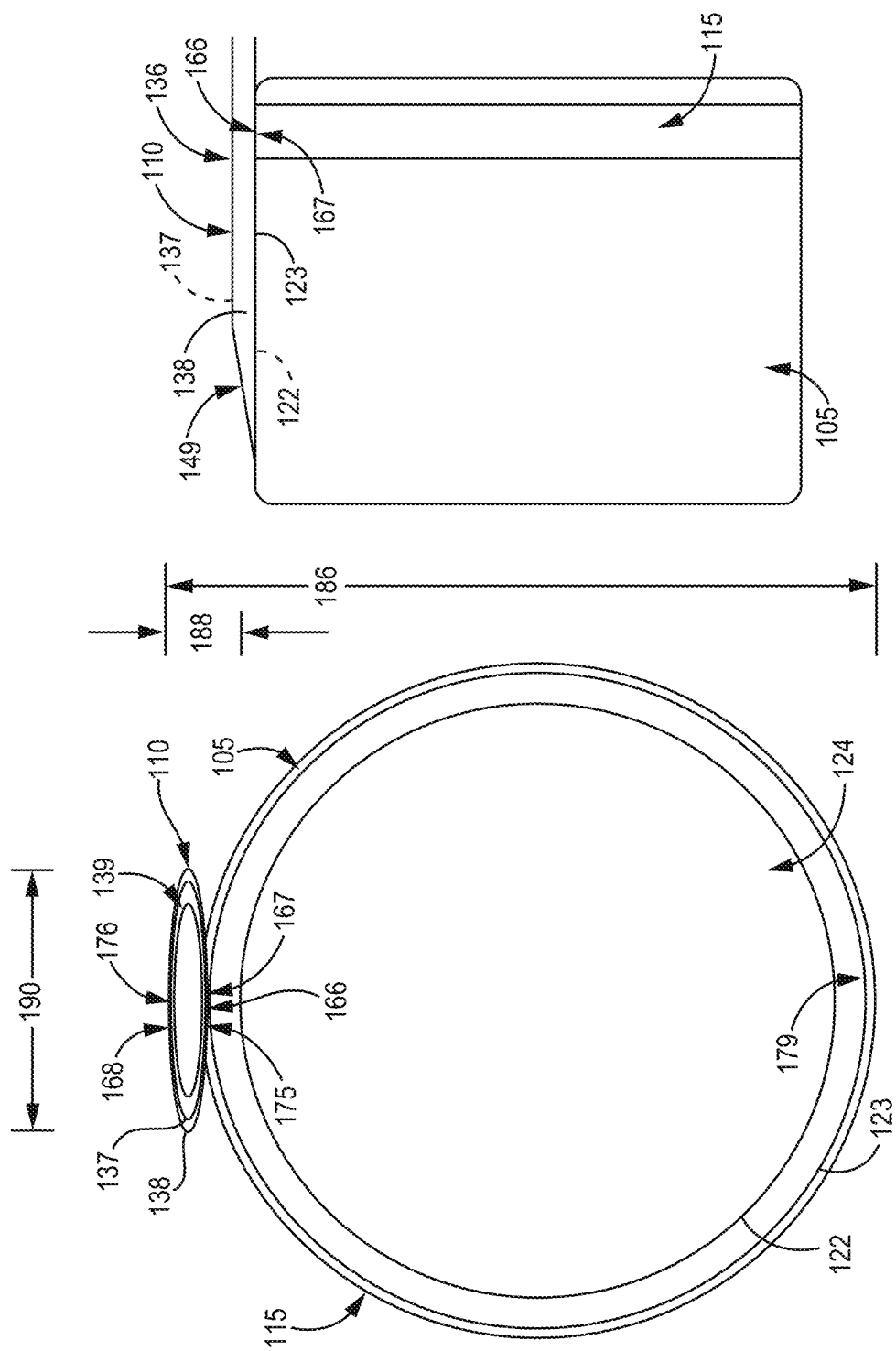
FIGS. 5A and 5B show the second sheath, of the sheath assembly embodiment of FIG. 1, in an exemplary collapsed state.

FIGS. 5A and 5B show the second sheath 110 in an exemplary collapsed state. FIG. 5A shows a cross-sectional view of the sheath assembly 100, taken along line A-A in FIG. 2, with the second sheath 110 in the collapsed state. FIG. 5B shows a close-up side elevational view of the sheath assembly 100 with the second sheath 110 in the collapsed state.

As shown in FIGS. 5A and 5B, when the second sheath 110 is in the collapsed state the profile of the sheath assembly 100 can be reduced as compared to the profile of the sheath assembly 100 when the second sheath 100 is in the expanded state, for instance as in FIGS. 4A and 4B. For example, as shown in FIG. 5A, the second sheath 110 can have a second cross-sectional height 188 in the collapsed state defined from the second portion 168 of the second sheath outer surface 138 to the first portion 166 of the second sheath outer surface 138. As also shown in FIG. 5A, the sheath assembly 100 can have a second overall cross-sectional height 186 defined from the second portion 168 of the second sheath outer surface 138 to the end portion 179 of the first sheath outer surface 123. Again, the second cross-sectional height 188 of the second sheath 110 and the second overall cross-sectional height 186 of the sheath assembly 100 are each measured in a direction perpendicular to the longitudinal axes 106, 111. Notably, when the second sheath 110 is in the collapsed state, the second cross-sectional height 188 of the second sheath 110 is less than the first cross-sectional height 187 of the second sheath 110 in the expanded state, for instance as in FIG. 4A. As a result, when the second sheath 110 is in the collapsed state the second overall cross-sectional height 186 of the sheath assembly 100 is less than the first overall cross-sectional height 185 of the sheath assembly 100 when the second sheath 110 is in the expanded state, for instance in FIG. 4A. For example, the second cross-sectional height 188 of the second sheath 110 can be between 1 mm and 4 mm, such as between 1.25 mm and 3.5 mm or between 1.6 mm and 2.7 mm, less than the first cross-sectional height 187 of the second sheath 110, likewise resulting in the second overall cross-sectional height 186 having this same reduction relative to the first overall cross-sectional height 185. This reduced profile of the sheath assembly 100 facilitated by the collapsible second sheath 110 can be useful in allowing the sheath assembly 100 to be deployed at the single access site 155.

In facilitating the reduced profile sheath assembly 100, when the second sheath 110 is in the collapsed state, such as shown in FIGS. 5A and 5B, the second sheath outer surface 138 can be brought closer to the first sheath outer surface 123. Specifically, in the illustrated embodiment, the second portion 168 of the second sheath outer surface 138 can be closer to the first sheath outer surface 123 when the second sheath 110 is in the collapsed state than when the second sheath 110 is in the expanded state. Thus, when the second sheath 110 transitions from the expanded state to the collapsed state the second portion 168 of the second sheath outer surface 138 can be brought closer to the first sheath outer surface 123. The reduction in the cross-sectional height (e.g., from height 187 to height 188) of the second sheath 110 can be accommodated by an increased cross-sectional width of the second sheath 110 in the collapsed state. Namely, the second sheath 110 can have a first cross-sectional width 189 when in the expanded state and a second cross-sectional width 190 when in the collapsed state, with the second cross-sectional width 190 being greater than the first cross-sectional width 189. Notably, by transferring the decrease in the cross-section height of the second sheath 110, from the height 187 to the height 188, to an increase in the cross-sectional width, from the width 189 to the width 190, of the second sheath 110 when the second sheath 110 is in the collapsed position acts to distribute the profile of the second sheath 110 in a manner suitable for deployment with the first sheath 105 by making the sheath assembly 100 better able to fit within the available space at the single access site 155 and vessel lumen 151.

In one example, the second sheath 110 can be configured such that in the collapsed state the first portion 175 of the second sheath inner surface 137 contacts the second portion 176 of the second sheath inner surface 137. For example, in the collapsed state where the first portion 175 of the second sheath inner surface 137 contacts the second portion 176 of the second sheath inner surface 137 a distance between the second portion 168 of the second sheath outer surface 138 and the first portion 166 of the second sheath outer surface 138 can be equal to or less than 2 mm, equal to or less than 1.5 mm, equal to or less than 1 mm, equal to or less than 0.75 mm, or equal to or less than 0.5 mm. Such a configuration of the second sheath 110 in the collapsed state could maximized the reduction in the profile of the sheath assembly 100. Regardless of whether the portions 175, 176 contact one another in the collapsed state, in certain embodiments when the second sheath 110 is in the collapsed state the second sheath 110 can be configured to add no more than 1.5 mm, such as no more than 1 mm, no more than 0.75 mm, no more than 0.67 mm, or no more than 0.5 mm to the height 186 of the sheath assembly 100.

Figure 6:
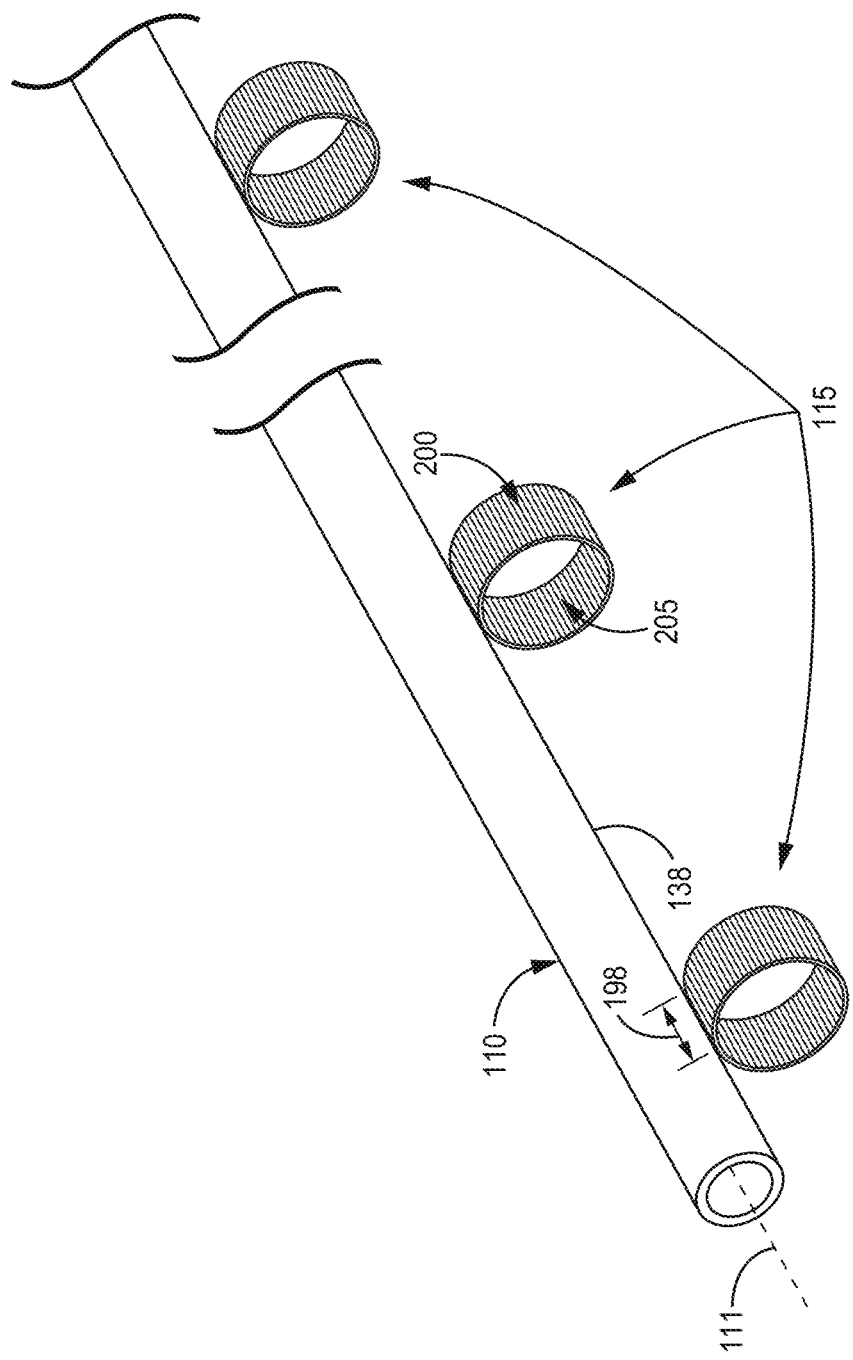
FIG. 6 is a perspective view of the second sheath, of the sheath assembly embodiment of FIG. 1, along with one embodiment of a number of attachment mechanisms.

FIG. 6 shows a perspective view of the second sheath 110 along with one embodiment of a number of attachment mechanisms 115. Each attachment mechanism 115 is secured to the second sheath outer surface 138 along a distance 198 of the second sheath outer surface 138. The attachment mechanisms 115 are spaced apart from one another on the second sheath outer surface 138 in a direction parallel to the second sheath longitudinal axis 111.

In the illustrated embodiment, each of the attachment mechanisms includes an elastic band 200. The elastic band 200 can be secured to the second sheath outer surface 138, for instance at the first portion 166 of the second sheath outer surface 138 such that other portions of the second sheath outer surface 138 (e.g., the second portion 168 of the second sheath outer surface 138) are free of the elastic band 200. The elastic band 200 can include an attachment mechanism surface 205 that is configured to be in contact with at least a portion of the first sheath outer surface 123. In this example, the attachment mechanism surface 205 forms a continuous loop configured to be in contact with the circumference of the first sheath outer surface 123. Though, in other embodiments, the elastic band 200 may have a break that forms a generally "C" shaped band. The attachment mechanism surface 205 can be configured to impart a frictional force at the first sheath outer surface 123 sufficient to prohibit relative movement between the first sheath 105 and the second sheath 110. For example, the attachment mechanism surface 205 can be configured to impart the frictional force at the first sheath outer surface 123 sufficient to prohibit relative movement between the first sheath 105 and the second sheath 110 upon an insertion force applied to the sheath assembly 100 of up to 15 lbf (pound-force), up to 12 lbf, up to 10 lbf, up to 8 lbf, up to 5 lbf, or up to 3 lbf. The insertion force applied at the sheath assembly 100 can vary depending on the application (e.g., the size of the first sheath 105 and/or the second sheath 110, the anatomical location of the access site 155, the vessel 150 within which the sheath assembly is advanced), and the attachment mechanism surface 205 can be configured to impart the frictional force at the first sheath outer surface 123 sufficient to prohibit relative movement between the first sheath 105 and the second sheath 110 upon the particular insertion force expected to be applied to the sheath assembly 100 in the particular application.

The elastic band 200 can be configured to stretch so as to increase the area defined within the elastic band 200 defined by the attachment mechanism surface 205. This can be useful in securing the second sheath 110 to the first sheath 105, since in some instances the first sheath outer surface 123 can have one or more geometric irregularities that necessitate the elastic band 200 to expand in order to pass over such irregularities. As such, the expandable nature of the elastic band 200 can be useful in allowing the second sheath 110 to be added on to a variety of first sheaths while also providing a sufficient securement force to maintain the second sheath 110 in place relative to the first sheath 105.

Figure 7:
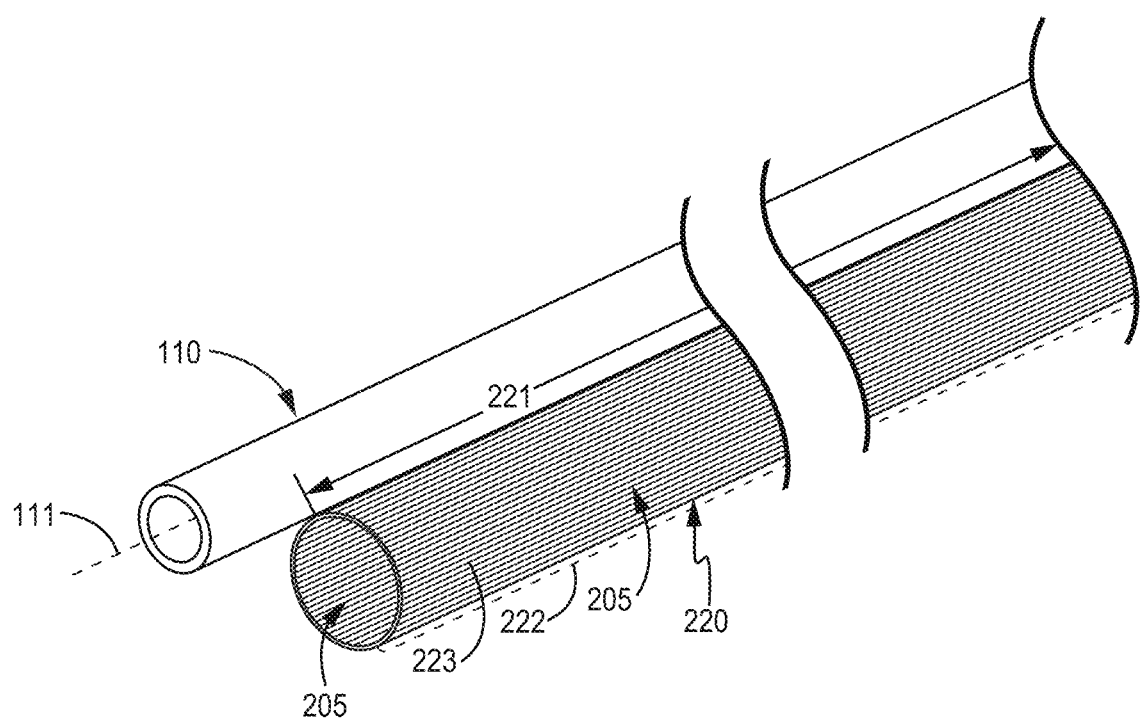
FIG. 7 is a perspective view of the second sheath, of the sheath assembly embodiment of FIG. 1, along with another embodiment of an attachment mechanism.

FIG. 7 shows a perspective view of the second sheath 110 along with another embodiment of an attachment mechanism 220. The attachment mechanism 220 can be similar, or the same as, the attachment mechanism 115 and/or 200 described previously herein except as illustrated and described here. For instance, the attachment mechanism 220 can include an elastic band as well as the attachment mechanism surface 205 as described previously.

The attachment mechanism 220 can have two main differences. The first is that the attachment mechanism 220 is in the form of a single, continuous attachment mechanism of a length 221 spanning substantially the length of the second sheath 110 from the second sheath first end portion 135 to the second sheath second end portion 136. Second, the attachment mechanism 220 can include a perforation 222. As such, the elastic band 205 of the attachment mechanism 220 can be configured to break along the perforation 222, such as when the first sheath 105 expands. The perforation can be included along an outer surface 223 of the elastic band 205 and extend in along the outer surface 223 in a direction parallel to the second sheath longitudinal axis 111. When the perforation 222 breaks, the band 205 can change from a continuous loop to a generally "C" shaped band, allowing the attachment mechanism 220 to accommodate the increase in size of the first sheath 105 while still maintaining the second sheath 110 secured to the first sheath 105.

The perforation 222 described in reference to the attachment mechanism 220 could be included and function in a similar, or same, manner at the attachment mechanism 115.

In other embodiments, the attachment mechanism can include a "C" shaped clip. This "C" shaped clip embodiment of the attachment mechanism can be configured to clip not the first sheath 105, for instance by applying a force to widen to opening in the "C" shaped clip as the attachment mechanism is placed around a portion of the first sheath 105 and then allowing the attachment mechanism to transition back to its "C" shaped configuration around the first sheath 105.

Figure 8:
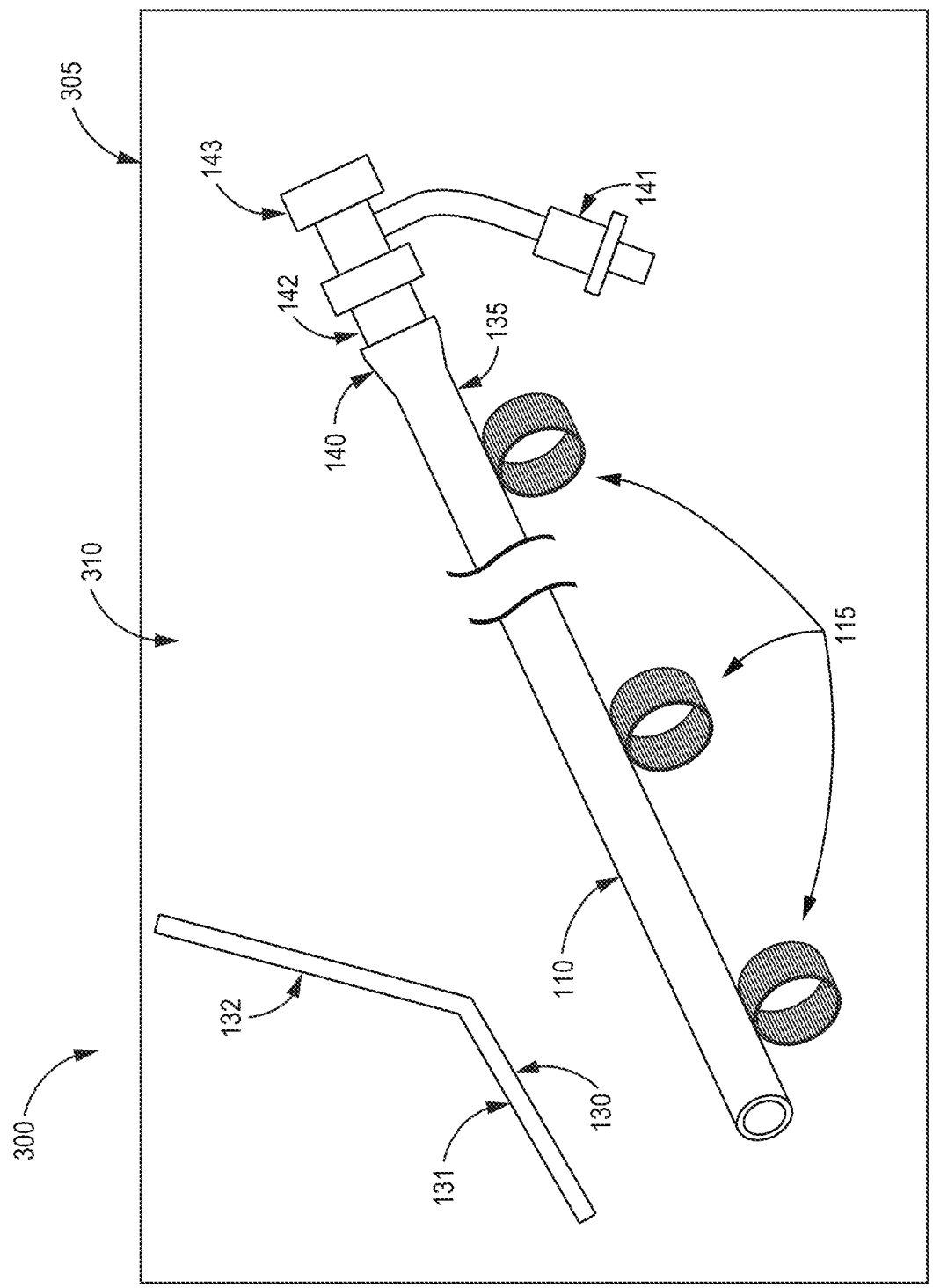
FIG. 8 is a schematic diagram of an embodiment of an add-on sheath kit that includes a packaging container defining a closed interior volume.

FIG. 8 shows a schematic diagram of an embodiment of an add-on sheath kit 300. The add-on sheath kit 300 includes a packaging container 305 defining a closed interior volume 310.

The closed interior volume 310 of the packing container 305 can include the second sheath 110, the proximal hub 140, and the clip 130. As described previously, the proximal hub 140 can include the flush port 141, the clip attachment interface 142, and the instrument insertion port 143. As also described previously, the clip 130 can include the first clip securement portion 131, configured to receive the second sheath 110, and the second clip securement portion 132, configured to receive the first sheath 105, to secure the sheaths 105, 110 together.

The add-on sheath kit 300 can be sealed to maintain the components within the closed interior volume 310 in sterile condition. In this way, the packaging container 305 can be opened and the components therein used to add the second sheath 110 to the first sheath 105, for instance to perform a procedure using the sheath assembly 100 via a single access site at the patient.

Figure 9:
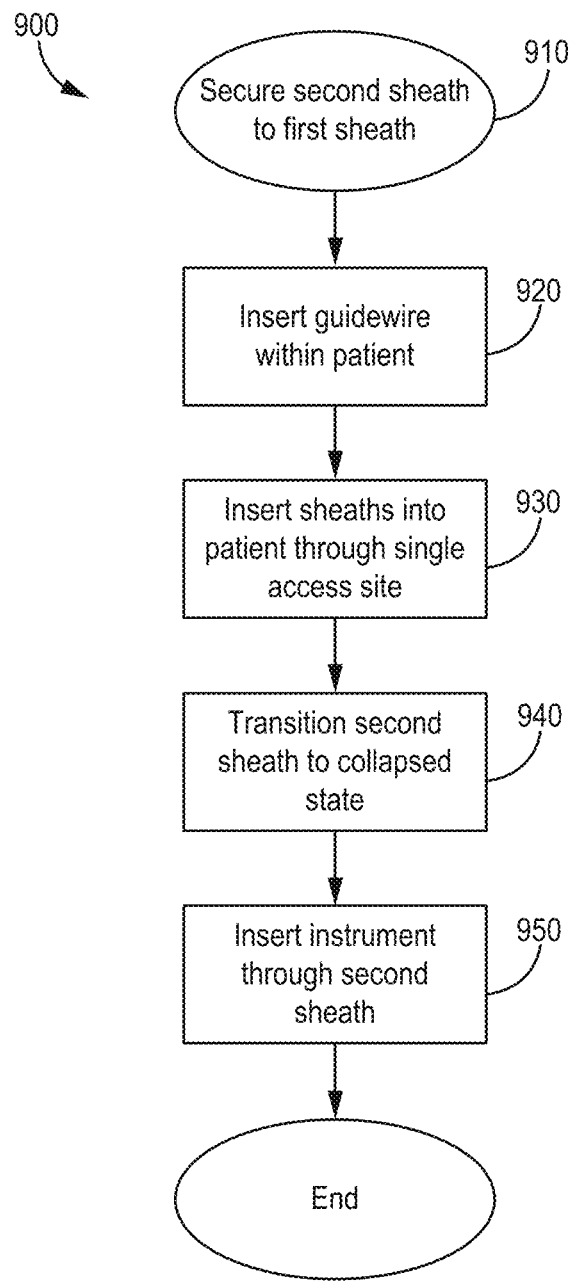
FIG. 9 is a flow diagram of an embodiment of a method of using a sheath assembly.

FIG. 9 shows a flow diagram of an embodiment of a method 900 of using a sheath assembly. The sheath assembly in the method 900 can be similar to, or the same as, the sheath assembly 100 disclosed herein.

At step 910, the method 900 includes the step of securing a second sheath to a first sheath to form the sheath assembly. The second sheath in the method 900 can be similar to, or the same as, the second sheath 110 disclosed herein. The first sheath in the method 900 can be similar to, or the same as, the first sheath 105 disclosed herein. Step 910 could include removing the second sheath from a packaging container and securing the second sheath to the first sheath via one or more attachment members, such as the attachment member(s) 115. This could include securing the attachment member around the outer surface of the first sheath while a majority of the outer surface of the second sheath remains free of the attachment member.

At step 920, the method 900 includes the step of inserting a guidewire within a patient. The guidewire can be inserted within a vessel lumen and advanced to a region of interest via a single access site at the patient. The guidewire can be inserted within the vessel lumen at step 920 after performing an interventional technique to puncture the target vessel to create an opening for guidewire insertion.

At step 930, the method 900 includes the step of inserting the sheath assembly—the secured together first and second sheaths—into the patient through a single access site. For example, the first sheath can be placed onto the guidewire and the first and second sheath can be interested together through the single access site into a vessel lumen and advanced through the vessel lumen to a region of interest.

At step 940, the method 900 includes the step of transitioning the second sheath from an expanded state to a collapsed state. For example, the second sheath can transition from the expanded state to the collapsed state when the second sheath comes into contact with the vessel wall defining the vessel lumen into which the first and second sheaths are inserted and advanced. The second sheath can transition to the collapsed state as a result of a force imparted in a first direction by the vessel wall on the second sheath outer surface and a force imparted in a second opposite direction by the first sheath outer surface. Transitioning the second sheath to the collapsed state can result in reducing the profile of the sheath assembly within the vessel lumen. This can be useful in allowing the sheath assembly to be used via a single access site at the patient.

At step 950, the method 900 includes the step of inserting an instrument through the second sheath. The instrument can be inserted through the lumen of the second sheath. The instrument can be, for instance, a diagnostic and/or interventional instrument, such as a diagnostic and/or interventional catheter (e.g., pigtail catheter and associated guidewire within the second sheath). The step of inserting the instrument through the second sheath can cause the second sheath to transition from the collapsed state toward the expanded state. Namely, inserting the instrument within the lumen of the second sheath can impart a force on the second sheath inner surface that counteracts the force imparted by the vessel wall on the second sheath outer surface so as to expand the second sheath outward away from the first sheath and toward the vessel wall. Notably, in this way, the second sheath can be transitioned from the collapsed state toward the expanded state only to the extent needed to accommodate the instrument within the second sheath lumen, thereby keeping a minimum necessary profile of the sheath assembly even when an instrument is actively being used in the second sheath lumen during a procedure. Accordingly, transitioning the second sheath between expanded and collapsed states can facilitate a reduced profile of the sheath assembly both during insertion and placement as well as during usage of the second sheath during a procedure, in turn allowing the sheath assembly to be capable of use via the single access site.

In some instances, the method 900 can further include, after step 950, steps of removing the instrument from the lumen of the second sheath and then removing the sheath assembly from the from the patient. For example, the step of removing the instrument from the lumen of the second sheath can transition the second sheath from the expanded state to the collapsed state. Namely, as described previously, without the instrument within the lumen of the second sheath the second sheath can be configured to collapse when in contact with the vessel wall as a result of the forces imparted on the second sheath outer surface by each of the vessel wall and the first sheath. Then, with the second sheath in the collapsed state, the sheath assembly can be removed from the vessel. Removing the sheath assembly from the vessel can include removing both of the first sheath and the second sheath together over the guidewire. With the second sheath in the collapsed state, the sheath assembly can be removed from the vessel while in a more reduced, compact profile relative to when the sheath assembly is at the region of interest and the instrument is within the lumen of the second sheath.

Various non-limiting exemplary embodiments have been described. It will be appreciated that suitable alternatives are possible without departing from the scope of the examples described herein. These and other examples are within the scope of the following claims.

What is claimed is:

1. A sheath assembly comprising:
a first sheath including a first sheath first end portion, a first sheath second end portion opposite the first sheath first end portion, a first sheath inner surface, and a first sheath outer surface opposite the first sheath inner surface, the first sheath inner surface defining a first sheath lumen extending along a first sheath longitudinal axis between the first sheath first end portion and the first sheath second end portion;
a second sheath including a second sheath first end portion, a second sheath second end portion opposite the second sheath first end portion, a second sheath inner surface, and a second sheath outer surface opposite the second sheath inner surface, the second sheath inner surface defining a second sheath lumen extending along a second sheath longitudinal axis between the second sheath first end portion and the second sheath second end portion; and
an attachment mechanism securing the second sheath to the first sheath such that a first portion of the second sheath outer surface interfaces with a portion of the first sheath outer surface,
wherein the second sheath includes a second portion of the second sheath outer surface that is opposite the first portion of the second sheath outer surface, wherein the second sheath is configured to transition between an expanded state and a collapsed state, the second portion of the second sheath outer surface being closer to the first sheath outer surface in the collapsed state than in the expanded state,
wherein the first sheath lumen defines a first sheath lumen cross-sectional area and the second sheath lumen defines an expanded state second sheath lumen cross-sectional area when the second sheath is in the expanded state, wherein the first sheath lumen cross-sectional area is greater than the expanded state second sheath lumen cross-sectional area, wherein the second sheath is biased to the expanded state, wherein the first sheath has a first hardness and the second sheath has a second hardness, and wherein the first hardness is greater than the second hardness,
wherein first sheath second end portion is a distal end of the first sheath, wherein the second sheath second end portion is a distal end of the second sheath, wherein the distal end of the second sheath is spaced apart from the distal end of the first sheath in a proximal direction, wherein the distal end of the second sheath defines a second sheath opening to the second sheath lumen, wherein the distal end of the second sheath is angled to define the second sheath opening extending in the proximal direction,
wherein the attachment mechanism comprises an elastic band attached to the first portion of the second sheath outer surface and extending around at least a portion of the first sheath outer surface, and wherein the elastic band includes a perforation, and wherein the elastic band is configured to break along the perforation when the first sheath expands.

2. The assembly of claim 1, wherein the sheath assembly is configured to be inserted within a vessel lumen, and wherein the second sheath is configured to transition from the expanded state to the collapsed state when the second portion of the second sheath outer surface comes into contact with a vessel wall defining the vessel lumen.

3. The assembly of claim 2, wherein the second sheath is configured to transition from the biased, expanded state to the collapsed state when forces are imparted on the second sheath by each of the vessel wall and the harder first sheath, and wherein the first sheath has a Rockwell hardness ranging from 70A to 100A.

4. The assembly of claim 1, wherein the sheath assembly is configured such that the second sheath is configured to transition from the expanded state to the collapsed state while the first sheath is maintained in a first sheath expanded state.

5. The assembly of claim 1, wherein the expanded state second sheath lumen cross-sectional area includes a diameter between 1 mm and 3 mm.

6. The assembly of claim 1, wherein the attachment mechanism secures the second sheath to the first sheath in a stacked arrangement.

7. The assembly of claim 1, wherein the second sheath includes a first portion of the second sheath inner surface adjacent to the first portion of the second sheath outer surface and a second portion of the second sheath inner surface adjacent to the second portion of the second sheath outer surface, and wherein the second sheath is configured such that in the collapsed state the first portion of the second sheath inner surface contacts the second portion of the second sheath inner surface.

8. The assembly of claim 1, wherein in the collapsed state a distance between the second portion of the second sheath outer surface and the first portion of the second sheath outer surface is equal to or less than 1 mm.

9. The assembly of claim 1, wherein the attachment mechanism comprises an elastic band attached to the first portion of the second sheath outer surface and extending around at least a portion of the first sheath outer surface.

10. The assembly of claim 9, wherein the second portion of the second sheath outer surface is free of the elastic band.

11. A sheath assembly comprising:
a first sheath including a first sheath first end portion, a first sheath second end portion opposite the first sheath first end portion, a first sheath inner surface, and a first sheath outer surface opposite the first sheath inner surface, the first sheath inner surface defining a first sheath lumen extending along a first sheath longitudinal axis between the first sheath first end portion and the first sheath second end portion;
a second sheath including a second sheath first end portion, a second sheath second end portion opposite the second sheath first end portion, a second sheath inner surface, and a second sheath outer surface opposite the second sheath inner surface, the second sheath inner surface defining a second sheath lumen extending along a second sheath longitudinal axis between the second sheath first end portion and the second sheath second end portion; and
an attachment mechanism securing the second sheath to the first sheath such that a first portion of the second sheath outer surface interfaces with a portion of the first sheath outer surface, wherein the second sheath includes a second portion of the second sheath outer surface that is opposite the first portion of the second sheath outer surface, wherein the second sheath is configured to transition between an expanded state and a collapsed state, the second portion of the second sheath outer surface being closer to the first sheath outer surface in the collapsed state than in the expanded state, and wherein the attachment mechanism comprises an elastic band attached to the first portion of the second sheath outer surface and extending around at least a portion of the first sheath outer surface, and wherein the elastic band includes a perforation, and wherein the elastic band is configured to break along the perforation when the first sheath expands.

12. The assembly of claim 1, wherein the attachment mechanism includes an attachment mechanism surface in contact with the first sheath outer surface, and wherein the attachment mechanism surface is configured to impart a frictional force at the first sheath outer surface sufficient to prohibit relative movement between the first sheath and the second sheath upon an insertion force applied to the sheath assembly of up to 12 lbf.

13. The sheath assembly of claim 1,
wherein the attachment mechanism secures the second sheath to the first sheath such that the first portion of the second sheath outer surface contacts the portion of the first sheath outer surface.

14. The sheath assembly of claim 11, wherein the first sheath lumen defines a first sheath lumen cross-sectional area and the second sheath lumen defines an expanded state second sheath lumen cross-sectional area when the second sheath is in the expanded state, wherein the first sheath lumen cross-sectional area is greater than the expanded state second sheath lumen cross-sectional area, wherein the first sheath has a first hardness and the second sheath has a second hardness, and wherein the first hardness is greater than the second hardness.

15. The sheath assembly of claim 11,
wherein first sheath second end portion is a distal end of the first sheath, wherein the second sheath second end portion is a distal end of the second sheath, wherein the distal end of the second sheath is spaced apart from the distal end of the first sheath in a proximal direction, wherein the distal end of the second sheath defines a second sheath opening to the second sheath lumen, wherein the distal end of the second sheath is angled to define the second sheath opening extending in the proximal direction, and wherein the attachment mechanism secures the second sheath to the first sheath such that the first portion of the second sheath outer surface contacts the portion of the first sheath outer surface.

* * * * *